United States Patent
Yonce

(10) Patent No.: US 6,597,942 B1
(45) Date of Patent: Jul. 22, 2003

(54) ELECTROCARDIOGRAPH LEADS-OFF INDICATOR

(75) Inventor: David J. Yonce, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 314 days.

(21) Appl. No.: 09/639,037

(22) Filed: Aug. 15, 2000

(51) Int. Cl.⁷ .................................................. A61B 1/00
(52) U.S. Cl. ...................................... 600/509; 600/512
(58) Field of Search ................................ 128/901, 905, 128/902; 600/508–512, 374, 375

(56) References Cited

U.S. PATENT DOCUMENTS 5,002,064 A * 3/1991 Allain et al. ................ 128/902
6,304,783 B1 * 10/2001 Lyster et al. .................. 607/63

* cited by examiner

*Primary Examiner*—Angela D. Sykes
*Assistant Examiner*—Omar A Khan
(74) *Attorney, Agent, or Firm*—Thomas J. Nikolai; Nikolai & Mersereau, P.A.

(57) ABSTRACT

A "leads-off indicator" for an ECG apparatus for indicating that one or more of a plurality of ECG electrodes is not properly affixed to a patient and that that obviates the need for a conventional high frequency drive signal, but instead, employs common mode input noise as a drive signal to a reference electrode such that if one of the electrodes defining an ECG vector is not properly affixed, an increase in the ambient noise on an ECG vector associated with the detached electrode occurs as a detectable event. A first algorithm is used to identify whether or not the reference electrode itself is properly affixed to the patient's right leg and, if so, the common mode signal presented to the remaining limb electrodes becomes unbalanced should one of the limb electrodes not be properly connected to the patient. An impedance balancing circuit is provided for developing signals allowing identification of a lose electrode when the ECG system does not utilize a right leg electrode as a reference.

7 Claims, 7 Drawing Sheets

ELECTROCARDIOGRAPH LEADS-OFF INDICATOR

BACKGROUND OF THE INVENTION

I. Field of the Invention

This invention relates generally to medical diagnostic apparatus, and more particularly to indicator circuitry included in an electrocardiograph (ECG) system for indicating whether one or more skin electrodes is properly connected to a patient.

II. Discussion of the Prior Art

Electrocardiography is the recording, usually from electrodes on the body surface, of the electrical activity of the heart during the cardiac cycle. Before each part of the heart contracts, there is a change in the membrane potential of the cardiac muscle cells, thus depolarization precedes contraction while repolarization follows and precedes relaxation. The potential differences can be recorded from electrodes on the body surface and the appearance of the recorded ECG depends on the sequence of depolarization and repolarization of the cardiac muscle mass and the position of the recording electrodes. A typical ECG utilizes 12 leads, such that 12 samples may be recorded with standard connections between the patient and the ECG machine. Interpretation of an ECG can provide a very detailed picture of heart function but, obviously to do this, requires considerable skill and experience. To properly understand and interpret ECG recordings, one must be able to understand the origin of the cardiac vectors, know the axes of the 12 ECG leads and appreciate the convention of normal vectors of depolarization and repolarization.

At rest, during diastole, the resting membrane potential cannot be detected without puncturing the cell with a microelectrode in that it does not cause any current to flow in the extracellular fluid. When the cardiac action potential propagates through the tissue, current flows in the extracellular fluid and the intracellular fluid, driven by the difference between membrane potentials in resting and depolarized zones. The potential difference recorded is a vector quantity in that it has both magnitude and direction and conventionally may be represented by an arrow pointed towards the resting membrane, i.e., in the direction of spread of electrical activity. The length of the arrow, of course, indicates the magnitude of the potential. By convention, if the electric vector is oriented toward the positive recording electrode, it is represented by an upward deflection of the ECG.

A triangle (Einthoven's Triangle) with the heart at its center is formed by placing recording limb electrodes on both arms and the left leg. The Einthoven's Triangle is generally represented as an equilateral in that the trunk of the patient is a uniform volume conductor and the heart acts a point source of electric vectors situated at its center. Vector I is defined as the potential difference between the right arm (RA) electrode and the left-arm (LA) electrode. Vector II is the potential difference between the RA electrode and the left-leg (LL) electrode. Vector III is the potential difference between the LA and the LL electrodes. According to Einthoven's Law, only two such leads are independent in that the third lead can be simply calculated from the other two.

An ECG system also employs chest leads. More particularly, in clinical routine use, six chest leads are used to record cardiac events under a single electrode with respect to an "indifferent" electrode. This reference point is formed by connecting the RA, LA and LL electrodes together with resistors, with the reference potential being appropriately the middle point of the Einthoven's Triangle, sometimes referred to as the Wilson Potential. Three additional vectors referred to as "augmented limb lead vectors" are based upon the Wilson Potential. The three limb electrodes, the six chest electrodes and three augmented limb electrodes total the twelve leads.

Many ECG machines incorporate a "lead-off indictor" to help identify a high-impedance ECG electrode patch. By providing such an indicator, a medical professional is able to quickly locate the source of a noisy signal and take appropriate steps to secure the lead patch to the skin of the patient. This reduces the amount of set-up and trouble-shooting time involved with an ECG measurement. Most conventional leads-off indicators use simple impedance measurements to determine whether an electrode is attached to the patient. Typically, the ECG machine applies a relatively high frequency (e.g., 30 KHz) drive signal to the patient through the electrode affixed to the patient's right-leg (RL) electrode. The ECG machine then measures this signal through the other input electrodes to determine whether the electrodes are properly attached by comparing the amplitude of the transduced 30 KHz signal to a predetermined reference.

This conventional approach of applying a high frequency drive signal to the RL electrode has drawbacks when several medical devices are used in conjunction with a given patient. Often several ECGs and monitors are connected to the patient at once, potentially causing errors in the leads-off indication if several such machines utilize the standard 30 KHz excitation signal. This problem can be significantly worse with certain pacemaker patients. Pacemakers from several manufacturers also utilize an excitation frequency near 30 KHz for deriving a rate-adaptive control signal based upon minute ventilation. The 30 KHz drive signal is applied by the pacemaker pulse generator circuitry as a carrier signal that is modulated by respiratory activity. The modulation signal is proportional to minute ventilation which is a parameter that varies predictably with the level of patient activity.

When ECG machines with prior-art style leads-off indicators are used with pacemaker patients having a minute ventilation-based rate adaptive pacemaker, the leads-off indicator can cause pacing at the upper-rate limit. In October 1998, the FDA's Center for Devices and Radiological Health issued an alert, warning physicians of this interaction.

In addition to the affects on the device, telemetry interference at 30 KHz can be significant and may cause the leads-off indicator to provide erroneous results. Thus, a need exists for a leads-off indicator for use in ECG equipment that can operate without interference from or with other medical devices being used with a given patient.

The present invention provides a leads-off indicator that does not require a 30 KHz excitation signal, but instead, utilizes information from the common-mode input noise to determine whether an electrode is connected to the patient. Nearly all ECG equipment operates in electrical environments with high levels of power line noise, 60 Hz being the dominant common-mode signal on the input electrodes for equipment used in the United States and 50 Hz in Europe. By comparing the relative noise between vectors, the RL output, and the common-mode input voltage, the noise level can be triangulated to reveal a high impedance electrode. By using the common-mode input noise instead of a 30 KHz drive signal, compatibility of the ECG leads-off indicator with minute ventilation-based rate adaptive pacemakers is provided, as is a high immunity to interference from telemetry or other monitors.

SUMMARY OF THE INVENTION

In accordance with the present invention, a leads-off indicator for an ECG machine may comprise a plurality of leads, each having a skin-contacting electrode at one end thereof adapted for attachment to a patient's body at predetermined locations to thereby define a plurality of ECG sensing vectors therebetween. One of the plurality of electrodes is selectively connectable to the patient's right leg as a reference. Sense amplifiers are connected to receive ECG signals and common-mode noise picked up by the skin-contacting electrodes, other than the RL electrode. Circuitry is provided for comparing a difference between an average of output signals from the sense amplifiers associated with the RA, LA, LL limb electrodes and signals derived from the RL electrode with a predetermined reference voltage for producing an output indicative of whether the RL electrode is properly connected to the patient. When it is determined that the RL electrode is properly connected to the patient, the circuitry is operative to apply a negative feedback signal as a drive to the RL electrode, where the feedback signal is proportional to the level of common-mode noise present on the electrodes other than the RL electrode. When it is determined that the RL electrode is not properly affixed to the patient, the resulting noise signal picked up by the RL electrode is used by the aforementioned circuitry used to compare the difference between an average of output signals from the sense amplifiers. Once the state of the RL electrode is confirmed, it is possible to identify which, if any, of the limb and chest electrodes are not properly secured to the patient.

DESCRIPTION OF THE DRAWINGS

The foregoing features, objects and advantages of the present invention will become apparent to those skilled in the art from the following detailed description of a preferred embodiment thereof when considered in conjunction with the accompanying drawings in which.

DESCRIPTION OF THE PREFERRED EMBODIMENT

Typical ECG machines use the right-leg (RL) electrode to provide negative feedback to the patient to greatly improve common-mode rejection. If the RL electrode is not properly attached to the patient, multiple channels can become noisy and corrupt the ECG traces. Leads-off indicators that rely upon excitation signals to determine lead status can develop an intermediate state if the RL electrode is not attached to the patient. If the excitation signal does not reach the patient, it will not be received by the input electrodes and will therefore improperly indicate that all of the input electrodes have a high impedance condition. The present invention improves over such prior art designs by determining when only the RL electrode is removed from the patient. This aids the user by providing a clear indication of the particular electrode that needs adjustment.

Figure 1:
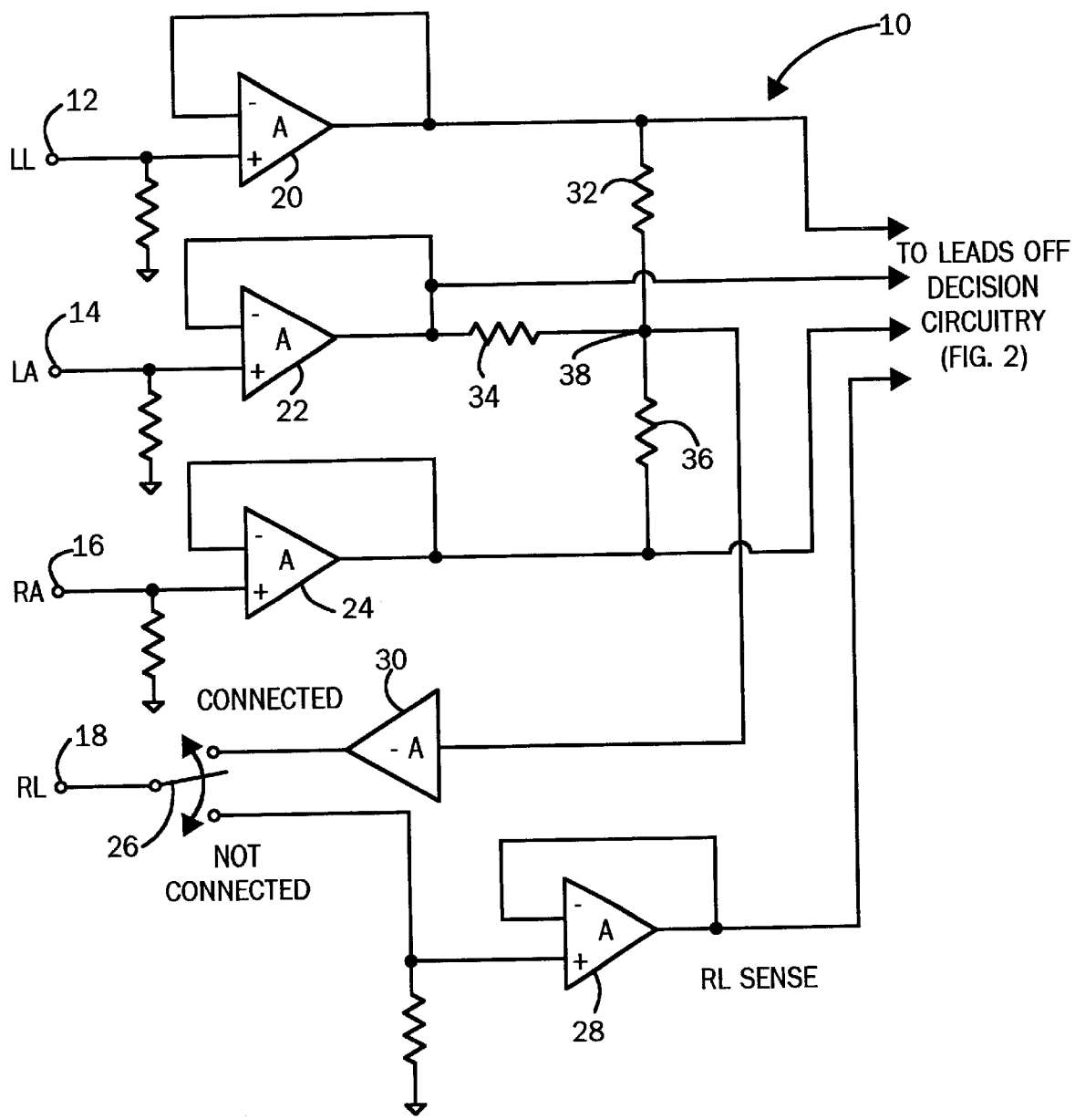
FIG. 1 is a circuit diagram illustrating the input stage for an ECG leads-off indicator.

As will be further explained, the leads-off indicator of the present invention utilizes two criteria to detect the status of the RL electrode, depending on whether it is currently properly attached to the patient or not. Indicated generally by numeral 10 in FIG. 1 is a circuit diagram of the ECG's input stage. A plurality of electrodes 12, 14, 16 and 18 are adapted to be attached to the patient, namely to the LL, LA, RA and RL, respectively. Each of the electrodes is connected by a lead to the non-inverting input of an operational amplifier. The LL electrode is connected to the non-inverting input of amplifier 20, the LA electrode to amplifier 22, the RA electrode to amplifier 24 and the RL electrode to a single-pole, double-throw electronic switching device 26. Depending upon the state of the switch 26, the RL electrode functions either as an input to operational amplifier 28 or as an output from an inverting amplifier 30.

Amplifiers 20, 22 and 24 have their output terminals coupled by resistors 32, 34 and 36 of equal value to a node 38, such that an average value of the outputs from the amplifiers 20, 22 and 24 is developed at that node and is applied as an input to the inverting amplifier 30.

Figure 2:
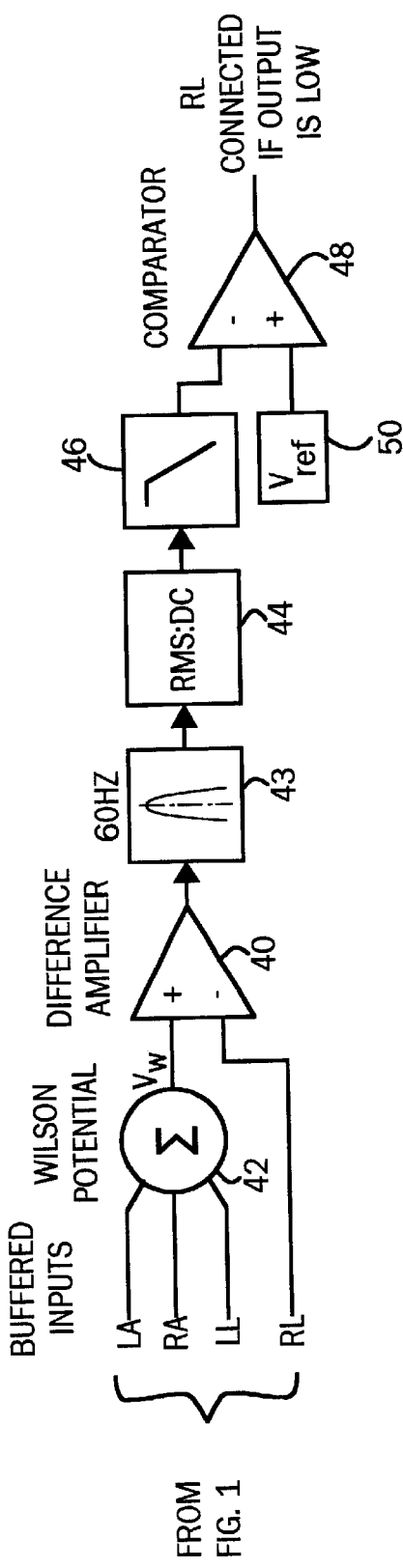
FIG. 2 depicts by means of a circuit diagram the decision circuitry used to determine if the right-leg electrode is properly connected to the patient.

When RL electrode 18 is not attached to the patient, the switch 26 disconnects the electrode from the output of inverting amplifier 30 and, instead, connects the RL electrode to the input of the sensing amplifier 28. As can be further seen from FIG. 1, the amplified input signals from electrodes LL, RA, LA and RL are applied as inputs to the leads-off decision circuitry illustrated in FIGS. 2 and 3.

Consider first the case where the ECG system is configured to operate without the RL electrode, but senses when the RL electrode is attached to the patient. The switch 26 (FIG. 1) automatically disconnects the RL electrode from the output of drive amplifier 30 and connects it to the sensing amplifier 28 when the RL electrode is not in use. The output from amplifier 28 is applied to the inverting input of a differential amplifier 40, while the sum of the outputs from amplifiers 20, 22 and 24 is applied by the summing circuit 42 to the non-inverting input of the differential amplifier 40. It can be seen that under these circumstances, the RL input voltage is subtracted from the average of the LL, LA and RA signals. This average is commonly referred to as the "Wilson Potential" ($V_W$). When the RL electrode is not properly connected to the patient, 60 Hz noise on the RL lead and $V_W$ will not be correlated in phase and amplitude due to the differences in skin-electrode impedances and coupling strengths. The amplitude differences between these two signals are often an order of magnitude or greater. However, once the RL electrode is properly attached to the patient, the 60 Hz signals will be very similar in terms of amplitude and phase, thus decreasing the difference between the inputs to the difference amplifier 40 to a small value. The 60-cycle noise emanating from a 60 Hz band pass filter 43 is converted to a DC signal by circuit 44 and then low pass filtered at circuit 46 to isolate the DC offset. The resulting DC signal level is applied to the inverting input of a comparator 48 which has a predetermined voltage reference value from a reference source 50 connected to its non-inverting input.

Once the difference between RL and $V_W$ drops below the threshold level established by reference 50, the output of the comparator is low indicative that the RL electrode is, in fact, properly attached to the patient. When this condition prevails, the system automatically throws the switch 26 to the output of the amplifier 30 and thereafter the decision circuit of FIG. 3 is employed to detect when and if the RL electrode becomes disconnected.

Figure 3:
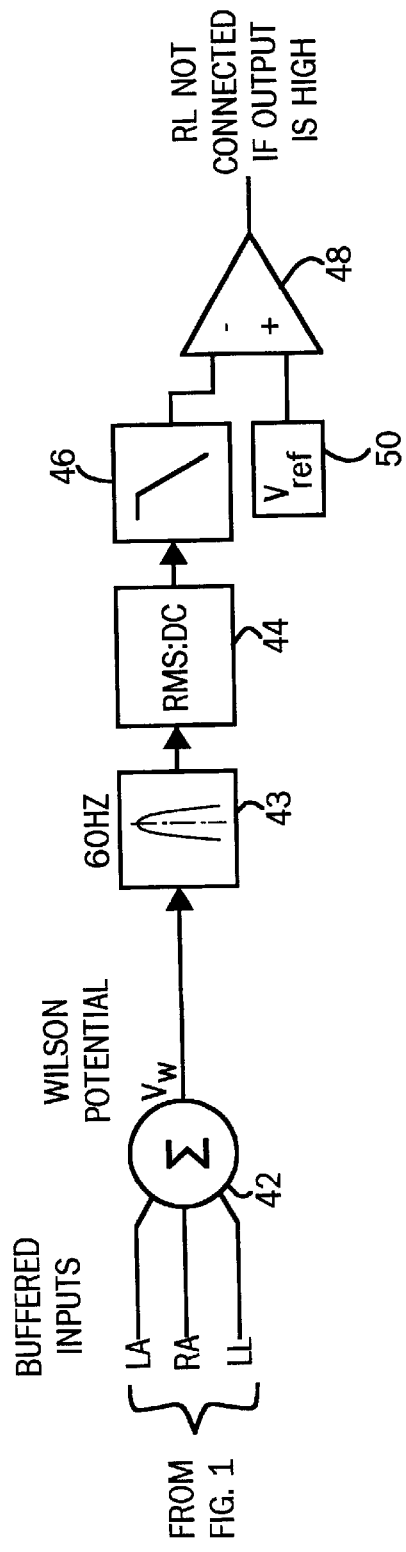
FIG. 3 is a similar circuit diagram of the decision circuitry used to determine if the right-leg electrode is not properly connected to the patient.

Referring, then, to FIG. 3, considering the RL electrode as being connected to the patient and functioning as an output driver, the level of average 60 Hz noise is extremely small, typically below 10 $\mu v$, in any of the input leads LA, RA or LL. Removing the RL electrode connection to the patient results in a drastic increase in the value of the output from the RMS-to-DC converter 44 causing the DC offset voltage at the output of the low pass filter 46 to exceed the reference voltage applied to the comparator 48, resulting in its output going high, indicating that the RL electrode is not connected to the patient. At this point, the RL electrode connection is configured by the switch 26 as a sensing input.

Figure 4:
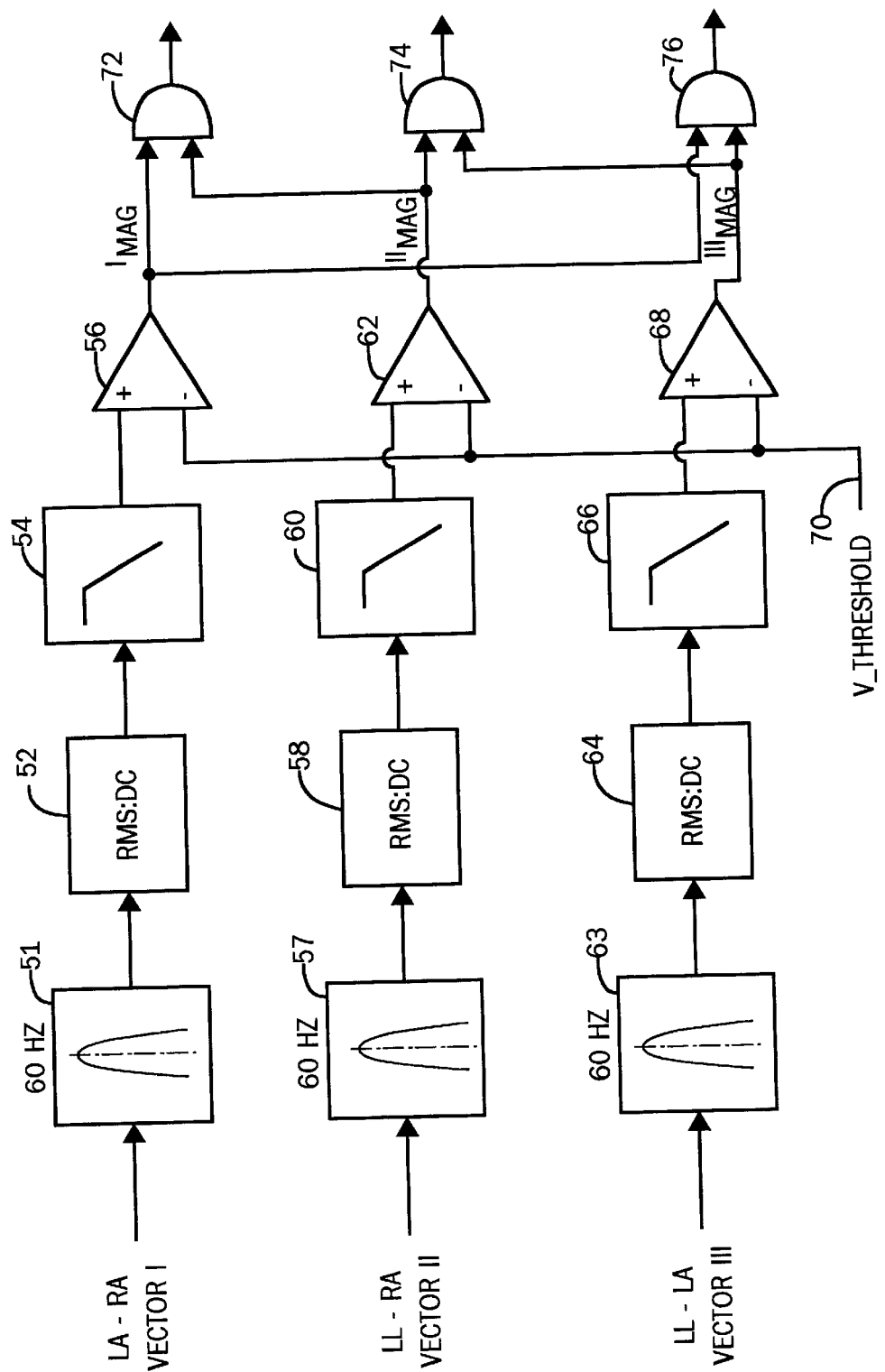
FIG. 4 is a block diagram of a leads-off algorithm for ECG sensing leads.

With the assumption that the RL electrode is properly connected to the patient, the circuit arrangement of FIG. 4 can be used to identify a particular one of the three limb electrodes, RA, LL or LA that is not properly connected to the patient. As already mentioned, with the RL electrode properly attached and thereby providing a negative feedback drive signal, the input 60 Hz noise is typically less than 10 $\mu v$ in amplitude. If one of the sensing electrodes is removed from the patient, and thus removed from the RL negative feedback, the noise transduced on the disconnected electrode will be significantly greater than the noise present on the other electrodes that are properly affixed. This causes greater 60 Hz noise on the vectors associated with the detached electrode, leaving one valid ECG vector. For example, first consider the case where the LA electrode comes loose from the patient while the LL, RA and RL electrodes maintain a good connection. Vector II (LL-RA) remains substantially free of noise since both electrodes defining Vector II are attached to the patient. Correspondingly, Vectors I (LA-RA) and III (LL-LA) become noisy.

The circuit of FIG. 4 shows on implementation for identifying the particular electrode that is not properly attached. The potential difference between the LA electrode and RA electrode comprises Vector I. The ambient noise is band pass filtered at 51 and the resulting noise signal is converted to a DC level by an RMS-to-DC converter 52 with any vestiges noise being removed by the low-pass filter 54, before being applied to the non-inverting input of a comparator circuit 56. Likewise, the potential difference between electrodes LL and RA define Vector II and the noise signal present is passed by band pass filter 57 and is converted to a DC level by RMS-to-DC converter 58. The output from converter 58 is low-pass filtered by circuit 60 and the resulting filtered output signal is applied to the non-inverting input of a comparator 62. The potential difference between electrodes LL and LA define Vector III and it, too, is band pass filtered by circuit 63 and converted to a DC level by RMS-to-DC converter 64. Its output signal is low-pass filtered by circuit 66 with the DC signal output from the filter 66 being applied to the non-inverting input of comparator 68. Each of the comparators 56, 62 and 68 have the same reference or threshold value applied over conductor 70 to the inverting inputs thereof If the outputs from comparators 56 and 62 are each high, AND gate 72 will be enabled and its output signal will be indicative that the electrode RA is not properly affixed to the patient. If the outputs from comparators 62 and 68 are simultaneously high, gate 74 is enabled which is indicative that electrode LL is not positively affixed to the patient. When the outputs from comparators 56 and 68 are simultaneously high, AND gate 76 will output a signal indicating that electrode LA is not properly attached to the patient.

While FIG. 4 illustrates a simple implementation of the detection algorithm in an analog domain, those skilled in the art will recognize that this algorithm may also be implemented in the digital domain. The algorithm can further be improved by incorporating a variable threshold for the comparators 56, 62 and 68 or by utilizing a digital signal processor to compare the magnitude values of each of the vectors.

Experiments have shown that if the disconnected electrode connects into the feedback network to the RL electrode (see FIG. 1), any phase difference between the noise picked up on the disconnected electrode and the noise transduced from the patient may cause an error in the feedback to the RL electrode, creating interference on a valid vector. However, the noise on the valid vector has been found to always remain much less than that on the other two vectors. Thus, by looking at the raw magnitude values, triangulation using the two highest magnitudes above a certain threshold level improves the detection criteria.

Figure 5:
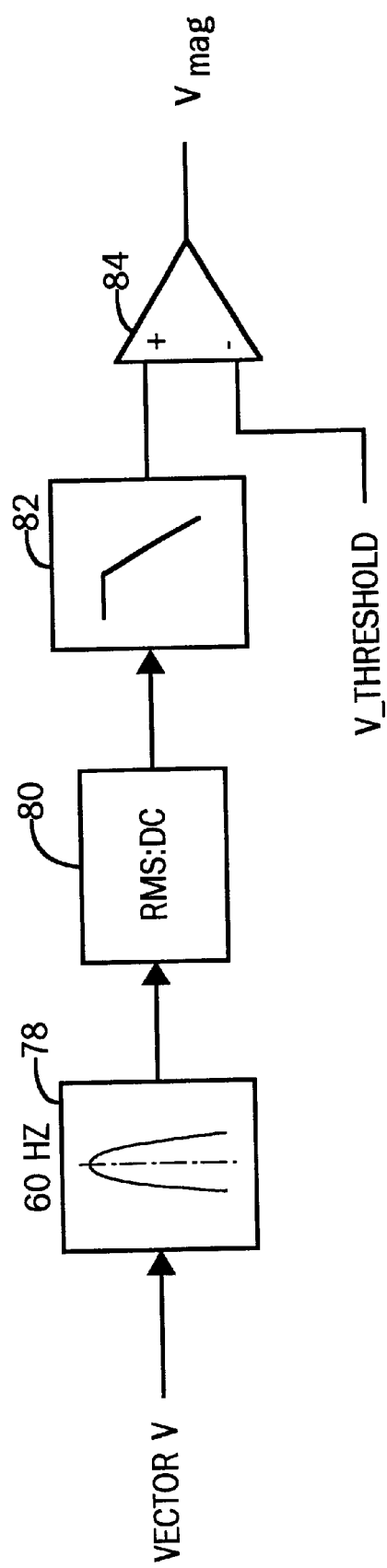
FIG. 5 is a block diagram of the decision circuitry used to detect the status of a chest electrode.

Once it is determined that the RA, LA and LL electrodes are properly affixed to the skin of the patient, the leads-off indicator of the ECG system can also indicate whether a chest electrode (V) is properly secured to the patient. ECG systems create a chest vector (V) by measuring the difference between the chest electrode V and the average signal at electrodes RA, LA and LL. Once the leads-off indicator confirms that all three limb electrodes are connected, the chest electrode can be detected by comparing the 60 Hz noise on each individual vector to a fixed threshold. FIG. 5 illustrates a block diagram of a circuit capable of making the determination for one chest electrode. This circuitry can be duplicated for as many chest vectors as are available in the system.

Referring to FIG. 5, the potential difference defining the chest vector V is band pass-filtered by filter circuit 78 that has a pass-band centered on 60 Hz. It should be understood, however, that if the ambient noise present in the environment is of a different frequency, e.g., 50 Hz as it is in Europe, then the filter 78 would be designed to pass that particular frequency and attenuate frequencies above and below the center value. The output from the band pass filter 78 is converted to a DC signal by RMS-to-DC converter 80 and, again, the output of that circuit is low pass filtered by circuit 82, allowing the DC signal proportional to noise level to be applied to the non-inverting input of operational amplifier 84 configured as a comparator. If the output from the comparator 84 exceeds the threshold potential applied to the non-inverting input of the comparator, the output from the comparator will be high indicative that the particular chest electrode is not properly affixed to the patient's chest.

It is desirable in equipment, such as pacemaker programmers, to provide an operational mode where the ECG feature thereof can function in the absence of a RL electrode being attached to the patient while still producing clean, relatively noise-free ECG signals. As will be explained in greater detail below, any skin-electrode impedance mismatch can be compensated for by incorporating an impedance balancing circuit into the system that automatically maximizes the common-mode rejection without requiring an RL electrode connection. Because the present invention provides for automatically detecting whether the RL electrode is properly attached to the patient, the ECG circuitry can automatically switch between two modes of operation for optimal performance under both conditions.

Figure 6:
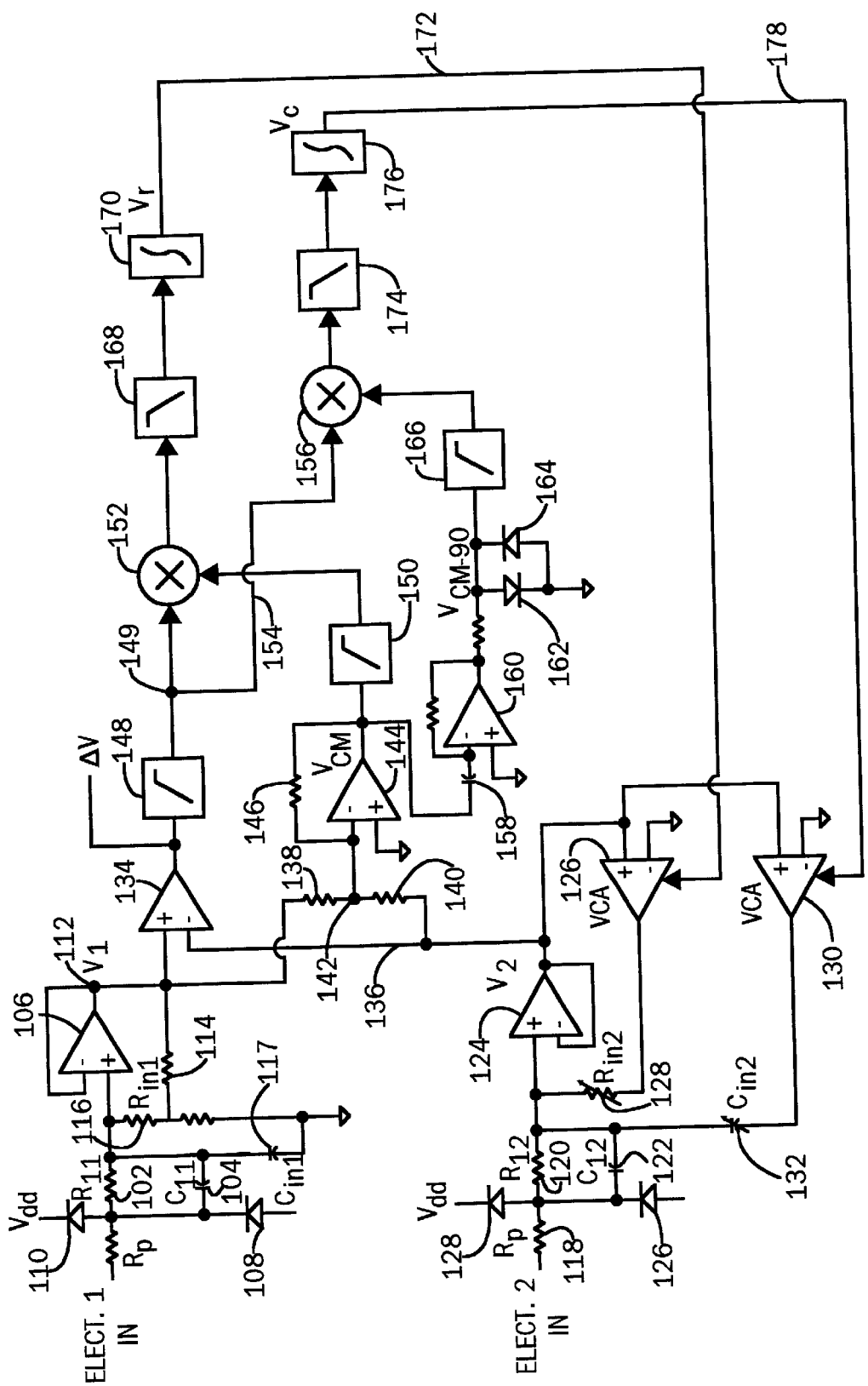
FIG. 6 is a circuit diagram of the impedance balancing circuitry used with the ECG inputs when the ECG system does not utilize a right-leg electrode.

FIG. 6 illustrates an impedance balancing circuit designed to minimize common mode noise between two ECG electrodes by effectively adjusting the resistive and reactive components of the input impedance associated with one of the two electrodes so as to effectively match the input impedance of the other. This circuit is similar in many respects to the automatic input impedance balancing circuit described in currently copending application Ser. No. 09/561,063, filed Apr. 28, 2000, and entitled "Improved Automatic Input Impedance Balancing For Electrocardiogram (ECG) Sensing Applications", the contents of which are hereby incorporated by reference. A first ECG electrode connects through a current limiting resistor 100 and a phase lead network comprising the parallel combination of resistor 102 and capacitor 104 to the non-inverting input of operational amplifier 106. Semiconductor diodes 108 and 110 provide voltage surge protection to the ECG electrodes by clamping noise to a predetermined reference potential applied to those diodes. The output $V_1$ appearing at node 112 is fed back through a feedback resistor 114 and an input resistor 116 to the non-inverting input of the operational amplifier 106. An input capacitance 117 is coupled between the non-inverting input of amplifier 106 and a source of reference potential (ground).

In a similar fashion, a second ECG electrode is coupled through a current limiting resistor 118 and a series phase lead network comprising resistor 120 in parallel with capacitor 122 to the non-inverting input of a second operational amplifier 124. Again, diodes 126 and 128 are included for voltage surge protection of the downstream electronics.

In the case of the operational amplifier 124, its feedback circuit includes a variable gain operational amplifier 126 whose output is coupled, via input resistor 128, to the non-inverting input of amplifier 124. The inverting input of voltage-controlled amplifier 126 is connected to ground. A second voltage controlled amplifier 130 is also connected in the feedback circuit of operational amplifier 124 and its output is coupled through input capacitance 132 to the non-inverting input of operational amplifier 124.

A differential amplifier 134 has its non-inverting input connected to the node 112 at the output of operational amplifier 106. The inverting input of differential amplifier 134 is tied to the output of amplifier 124, via conductor 136. A voltage divider, including series connected resistors 138 and 140, is coupled between the output terminals of the amplifiers 106 and 124. The common terminal 142 between the voltage divider resistors 138 and 140 is directly connected to the inverting input of a buffer amplifier 144 whose non-inverting input is tied to ground. A feedback resistor 146 connects the output terminal of amplifier 144 to its inverting input.

The outputs from the differential amplifier 134 and the buffer amplifier 144 are connected through high-pass filters 148 and 150, respectively, with the resulting filtered output signals being applied to a multiplier circuit 152.

The output from the high-pass filter 148 is applied, via conductor 154, to a second multiplier circuit 156. Multiplier circuit 156 receives its second input through a 90° phase shift circuit that includes a phase shift capacitor 158, a feedback amplifier 160, oppositely polled clamping diodes 162 and 164. The output from the amplifier 160 is high-pass filtered by filter circuit 166 and then applied to a second input of the multiplier circuit 156. The circuit 156 multiplies a 90° phase shifted version of the common mode signal developed at the output of buffer amplifier 144 by the high-pass filtered $\Delta V$ signal at node 149.

The output from multiplier 152 is low-pass filtered by circuit 168 whose output is then applied to an integrator circuit 170. The resulting output signal $V_r$ is fed back over conductor 172 to the control input of the voltage controlled amplifier 126. Likewise, the phase shifted version of the common mode signal outputted by multiplier 156 is low-pass filtered by circuit 174 and the resulting DC offset signal is integrated by circuit 176 whose output passes over conductor 178 to the control input of the voltage-controlled amplifier 130.

The impedance balancing circuitry illustrated in FIG. 6 is configured to match any series impedance mismatches that may be present between electrode 1 and electrode 2. The circuit attempts to adjust the effective resistance and reactance of impedance elements 128 and 132 so that the attenuation and phase shift at the non-inverting input of amplifiers 106 and 124 will be equal for common mode noise. As an example, let it be assumed that the series impedance on electrode 1 is greater than that of electrode 2. This causes a greater attenuation of the voltage applied to the non-inverting input of amplifier 106 than at the corresponding input of amplifier 124. Hence, when the outputs from these two amplifiers ($V_1$ and $V_2$) are measured differentially by differential amplifier 134, a negative going signal $\Delta V$ will be outputted by the differential amplifier 134. Likewise, if it is assumed that there is a common mode 60 Hz noise signal on electrodes 1 and 2, the differential amplifier 134 will be a 60 Hz signal that is 180° out of phase with respect to the common mode signal.

The feedback circuitry coupling the output from the differential amplifier 134 to the voltage controlled amplifier 126 takes an average of the input signals $V_1$ and $V_2$ which is the common mode signal that is developed across the voltage divider 138–140 and which is buffered by amplifier 144 to become the signal $V_{cm}$.

The common mode signal, $V_{cm}$, is high-pass filtered at 150 to remove any DC offset, and is multiplied by the differential signal $\Delta V$. In the case of 60 Hz noise, in that it is 180° out of phase, the output from the multiplier 152 will be of a 120 Hz frequency with a negative DC offset.

The DC offset is low-pass filtered at 168 to remove the AC signal component leaving only the DC offset which is integrated by circuit 170 to yield the control signal $V_r$. With a negative DC input signal to the integrator, $V_r$ will begin moving toward the negative rail with a slope depending on the magnitude of the DC voltage input. This signal drives the voltage-controlled amplifier 126 which is essentially configured in a boot strap relation with the input resistor 128 so that the voltage controlled amplifier 126 is varying the attenuation of amplifier 124. Recalling that the original assumption has been that the skin electrode impedance or series impedance is greater on electrode 1 than on electrode 2, there would be greater attenuation on the output from amplifier 106 than that on amplifier 124. So that the common mode amplitudes at each input will be equal, the effective resistance of resistor 128 must be decreased. The effect of the feedback signal $V_r$ is to decrease the gain of amplifier 126, which functions to attenuate or decrease the effective resistance of input resistor 128 to cause it to become matched to the input resistance 116 of amplifier 106.

The feedback circuitry producing the control signal $V_c$ at the output of integrator 176 performs a similar function to the quadrature signal by altering the effective reactance of capacitor 132. Hence, for any complex impedance that is present at the inputs of amplifiers 106 and 124, the feedback network described functions to balance the two.

Having described the impedance balancing network of FIG. 6, consideration will next be given as to how it may be used to provide a leads-off indication when the ECG system does not employ a RL electrode. If one of electrode 1 or electrode 2 is not properly connected to the patient, there is an infinite impedance to the common mode signal and the feedback circuit in the impedance balancing network will be unable to produce a balance. The feedback signals $V_r$ and $V_c$ will go all the way to the rail voltage of the integrators 170 and 176 and will remain at that level. Further, it will be unable to null out the 60 Hz noise. If either the $V_r$ and $V_c$ goes to either its minimum or maximum value, it is indicative that a lead is off The impedance balancing circuit is duplicated. Electrode 1 in FIG. 6 may be the RA electrode while electrode 2 may be the LL electrode. In the duplicated circuit, electrode 1 may be the RA electrode and electrode 2, the LA electrode. Under the assumptions made, the respective signals $V_r$ and $V_c$ feedback signals are driving the LL and LA electrodes. Thus, if either signals $V_r$ and $V_c$ that is driving the LL electrode goes to its rail, it would be known that vector II cannot be nulled out. Similarly, if signals $V_r$ and $V_c$ for the LA is also sitting at the rail, then vector I cannot be nulled out. By triangulation, then, the particular unattached electrode is identified.

Figure 7:
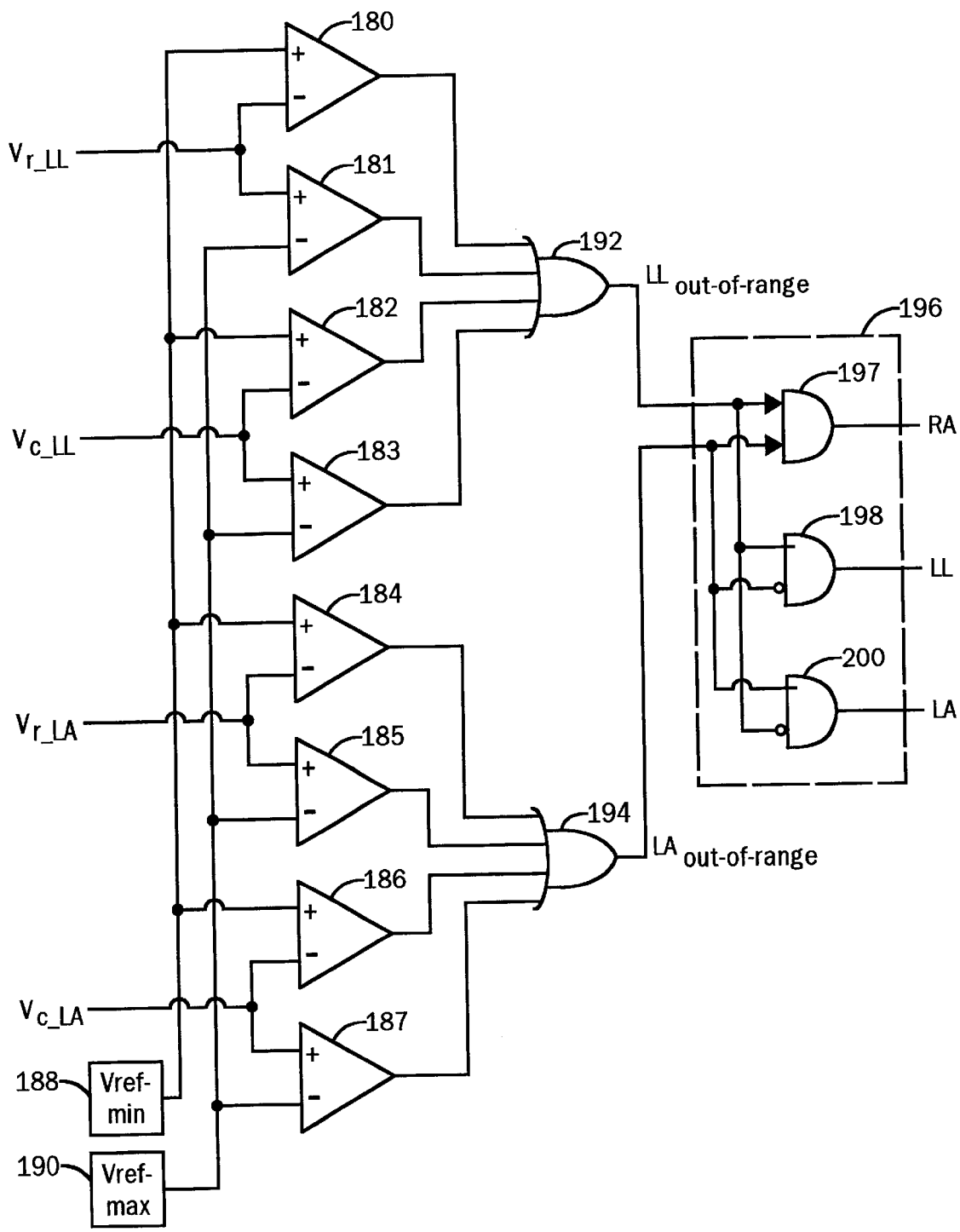
FIG. 7 is a logic diagram of identification circuitry used with the impedance balancing circuitry of FIG. 6 to provide an indication of a particular electrode that is not in proper contact with the skin of the patient.

FIG. 7 illustrates a block diagram of the decision circuitry used to determine which electrode impedance is out of range and, therefore, which of the electrodes is not properly affixed to the patient. The decision circuitry includes a plurality of comparators 180–187, with the even numbered comparators having their non-inverting inputs connected to a minimum reference voltage 188. The odd numbered comparators in FIG. 7 have their inverting input terminals connected to a reference source 190 which is the maximum rail voltage for the integrator circuits of FIG. 6. The signal developed at the output of the integrator 170 associated with the LL electrode is connected to the inverting input of comparator 180 and to the non-inverting input terminal of comparator 181. The signal output from integrator 176 in FIG. 6 for the LL electrode is connected to the inverting input of comparator 182 and the non-inverting input of comparator 183. The output from integrator 170 associated with the LA electrode is applied to the inverting input of comparator 184 and to the non-inverting input of comparator 185. Finally, the output of integrator 176 of FIG. 6 for the LA electrode is connected to the inverting input of comparator 186 and to the non-inverting input of comparator 187. The outputs from comparators 180–183 are connected as inputs to an OR gate 192 while the outputs from the comparators 184–187 are connected to inputs of an OR gate 194. Thus, if the signal signals $V_r$ or $V_c$ reaches the rail potential established by reference sources 188 and 190, one of the OR gates 192 or 194 will output an out-of-range signal. A translator shown enclosed by broken line box 196 is then used to identify the particular electrode that is not properly connected to the patient. If OR gates 192 and 194 are both outputting high signals, AND gate 197 is enabled and it is the RA electrode that is improperly secured to the patient. If only OR gate 192 is producing a high output signal, then AND gate 198 will be enabled to indicate that the LL electrode is disconnected. If only OR gate 194 is producing an out-of-range signal, AND gate 200 will output a high signal indicating that the LA electrode is not properly attached.

Figure 8:
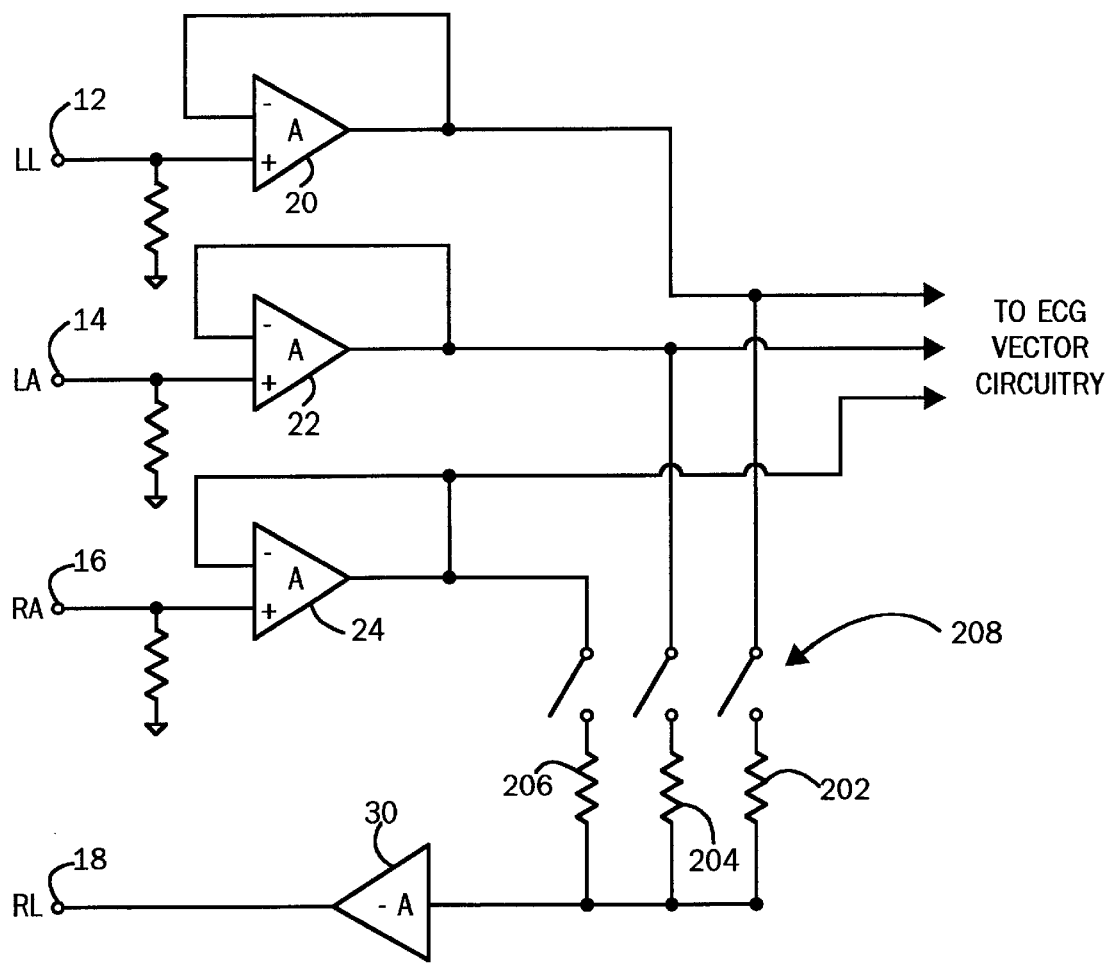
FIG. 8 is a block diagram of an arrangement for use in ECG equipment for eliminating a contribution of a disconnected electrode to the right leg feedback path.

While the cardiac rhythm management device programmer for which the present invention has been developed permits up to four sensing electrodes (RA, RL, LL and V), clinicians may sometimes opt to use a limited subset of available electrodes. In a case where only two of the three limb electrodes and the RL electrode are attached to the patient, the non-attached third limb electrode can couple noise into a displayed vector, via the RL feedback path. Besides alerting the clinician of a disconnected electrode, the ECG system can utilize the leads-off indicator to automatically eliminate the contribution of the disconnected electrode to the RL feedback path, thereby maintaining optimum performance regardless of the electrode configuration. To better understand how this is achieved, reference is made to the block diagram of FIG. 8. Here, the input amplifiers 20, 22 and 24 associated respectively with the LL electrode 12, the LA electrode 14 and the RA electrode 16 have their output terminals adapted for connection through resistors 202, 204 and 206 of equal value by way of an electronic single-pole, single-throw switch 208 to the input of the feedback amplifier 30. Consider first the case where a clinician only wishes to display vector II, i.e., the potential difference between the LL and RA electrodes. If the ECG system is set up to allow viewing of multiple vectors, say, the three limb leads that provide vectors I, II and III, the switches 208 are closed such that the average of the LL, LA and RA inputs are fed back through amplifier 30 and the RL electrode to the patient so as to provide attenuation of the common mode signal. In a case where the clinician only wants one ECG vector, he/she may only connect up the LL and RA electrodes to the patient. This would leave the LA electrode unattached and it would not be at the same potential as the LL and RA electrodes. Hence, there will be a large voltage difference. This would be due to the fact that the LA electrode could be coupling noise into the RL feedback signal thereby increasing the level of noise on the ECG output. Since under the assumed conditions, LL and RA electrodes now will not see the same level of noise, there is no longer a common mode signal between them. In an automatic ECG configuration, the leads-off indicator of the present invention functions to determine that a lead is not properly connected and removes the contribution of the non-connected electrode to the RL feedback. Where the LA electrode is not being used, the connection between the unused electrode and the RL feedback is interrupted by one of the switches 208 so that the noise performance is maintained automatically.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A leads-off indicator for an ECG apparatus comprising:
   (a) a plurality of leads, each having a skin contacting electrode at one end thereof adapted for attachment to a patient's body at a predetermined location, to define a plurality of sensing vectors therebetween, one of said electrodes selectively connectable to the patient's right leg;

(b) a plurality of sense amplifiers individually connected to receive ECG signals and common-mode noise picked up by the skin contacting electrodes, but not ECG signals and common-mode noise from said one of said electrodes; and (c) means for comparing a difference between an average of output signals from said plurality of sense amplifiers and signals derived from said one of said electrodes with a predetermined reference voltage for producing an output indicative of whether the said one of said electrodes selectively connectable to the patient's right leg is properly connected to the patient.

2. The leads-off indicator of claim 1 and further including means for applying a negative feedback signal to the said one of said electrodes when the output of the comparing means indicates that the said one of said electrodes is properly affixed to the patient.

3. The leads-off indicator of claim 2 and further including switching means for selectively connecting said negative feedback signal as a drive signal to the said one of said electrodes when the output of the comparing means indicates that the said one of said electrodes is properly affixed to the patient and for connecting the said one of said electrodes to the comparing means when the output of the comparing means indicates that the said one of said electrodes is not properly affixed to the patient.

4. A leads-off indicator for an ECG apparatus comprising:

(a) a plurality of leads, each having a skin contacting electrode at one end thereof adapted for attachment to a patient's body at a predetermined location, to define a plurality of sensing vectors therebetween, one of said electrodes selectively connectable to the patient's right leg;

(b) a plurality of sense amplifiers individually connected to receive ECG signals and common-mode noise picked up by the skin contacting electrodes, but not ECG signals and common-mode noise from said one of said electrodes;

(c) a difference amplifier having positive and negative input terminals and an output terminal, the positive input terminal connected to receive a signal proportional to the average of output signals from said plurality of sense amplifiers, the negative input terminal connected to receive the signals derived from the said one of said electrodes, the output terminal carrying a signal proportional to the difference therebetween; and (d) a signal comparator for comparing a signal related to the signal carried by the output of the difference amplifier to a predetermined reference.

5. The leads-off indicator of claim 4 and further including signal processing circuitry disposed between the output terminal of the difference amplifier and the signal comparator.

6. The leads-off indicator of claim 5 wherein the signal processing circuitry produces a DC signal related to ambient noise picked up by the skin contacting electrodes.

7. The leads-off indicator of claim 4 and further including means for comparing an ambient noise level of each of the plurality of sensing vectors to determine which, if any, of the skin contacting electrodes, other than the said one of said electrodes, is not in contact with the patient.

* * * * *